(12) United States Patent
Elist

(10) Patent No.: US 8,986,193 B1
(45) Date of Patent: Mar. 24, 2015

(54) PENILE IMPLANT

(71) Applicant: James Elist, Beverly Hills, CA (US)

(72) Inventor: James Elist, Beverly Hills, CA (US)

( * ) Notice: Subject to any disclaimer, the term of this patent is extended or adjusted under 35 U.S.C. 154(b) by 0 days.

(21) Appl. No.: 13/714,198

(22) Filed: Dec. 13, 2012

(51) Int. Cl.
*A61F 5/00* (2006.01)
*A61F 2/26* (2006.01)

(52) U.S. Cl.
CPC ........................................ *A61F 2/26* (2013.01)
USPC ............................................................ 600/38

(58) Field of Classification Search
CPC . A61F 2/26; A61F 2/0063; A61F 2002/0068; D04B 21/12; D10B 2509/08
USPC .................................................... 600/38–41
See application file for complete search history.

(56) References Cited

U.S. PATENT DOCUMENTS

| | | | |
|---|---|---|---|
| 3,455,301 A * | 7/1969 | Clark | 600/41 |
| 4,204,530 A * | 5/1980 | Finney | 600/40 |
| 4,532,920 A * | 8/1985 | Finney | 600/40 |
| 6,537,204 B1 * | 3/2003 | Elist | 600/40 |
| 6,749,558 B1 * | 6/2004 | Brintle | 600/38 |
| 7,584,757 B2 * | 9/2009 | Krakovsky | 128/898 |
| 7,628,812 B2 * | 12/2009 | aWengen et al. | 623/10 |
| 2003/0212463 A1 * | 11/2003 | Seo | 623/23.72 |

FOREIGN PATENT DOCUMENTS

KR 0136797 * 11/1998 ............. 600/40

* cited by examiner

*Primary Examiner* — Samuel Gilbert
(74) *Attorney, Agent, or Firm* — Patent Law & Venture-Group; Gene Scott

(57) ABSTRACT

A penile implant having a body with a circular and linear elongated wall having an outer and an inner exterior surfaces. The body tapered from a larger to a small diameter between opposing longitudinal ends. The elongated wall tapered diametrically from a thicker to a thinner wall thickness between a top position and two opposing longitudinally extensive edges. Net fabric sheets imbedded below surfaces of the outer and the inner exterior walls wherein the net fabric sheets prevent the body from creasing.

2 Claims, 3 Drawing Sheets

PENILE IMPLANT

BACKGROUND

This disclosure relates to regenerative medicine and particularly to a surgical implant procedure and device for the enhancement and appearance of the human penis, and more particularly to a penile implant enabling a non-functioning penis to fulfill normal sexual function. A patent, U.S. Pat. No. 6,537,204 was issued to James Elist on Mar. 25, 2003 for a similar implant and the subject matter of this patent is incorporated by reference hereinto in its entirety. The presently described implant of this disclosure advances the state of the art over the '204 references as will be described herein.

Regenerative medicine is the process of replacing or regenerating human cells, tissues or organs to restore or establish normal function. This field holds the promise of regenerating damaged tissues and organs in the body by replacing damaged tissue and/or by stimulating the body's own repair mechanisms to heal previously irreparable tissues or organs. Regenerative medicine refers to a group of biomedical approaches to clinical therapies that may involve the use of stem cells and implantation devices as well as other approaches. Examples include the injection of stem cells or progenitor cells (cell therapies); the induction of regeneration by biologically active molecules administered alone or as a secretion by infused cells and transplantation of in-vitro grown organs and tissues. For example, in abdominal wall reconstruction such as inguinal hernia repair, biologic meshes have been used successfully. When an organ, such as the human penis, is physically damaged or becomes functionally impotent, the implantation of structural elements is sometimes desirable. A prior known approach is disclosed in U.S. Pat. No. 6,537,204, Mar. 25, 2003, to the present discloser and is hereby incorporated in its entirety herein. The present application discloses and claims certain non-obvious and novel, critical improvements as will be described and shown herein.

BRIEF SUMMARY AND OBJECTIVES

The present disclosure describes an implant, its use, method of forming and method of implantation which results in restoring the use of the human penis after damage or atrophy has occurred or congenital deformities, penile dysmorphia. The penile implant described herein is formed as a unitary body having an elongated aspect in a longitudinal direction and a circular aspect in a transverse direction, the body having a hollow core and mesh layers under both outside and inside exterior surfaces. It has been found that when the inside exterior surface, as taught in the '204 reference, is faced with a mesh layer, the implant tends to fold, crease and ultimately break or crack along a top surface rendering a partial or even total dysfunction of the implant. With the addition of a top mesh layer, there is no cracking or splitting of the top surface. This is critical to the functional aspects of the implant enabling long-term use and shape maintenance. Another improvement of the presently disclosed implant is that it is molded in one unitary piece. Prior to the year 2003 it was believed that the implant must be inserted into the penis with first one half seated into place and then, once that was successfully completed, only then could the second half be seated, a two-step process using a two piece implant as described in the '204 reference. The advantages of the present improved implant is that it considerably reduces the time of exposure of the pubic shaft since suturing is minimized limited only to connection of the implant to the glans penis. Furthermore, the monolithic shape of the implant provides a great improvement is establishing a more realistic final shape and utility. With advances in the physical characteristics of silicon rubber, such as its elasticity and resiliency, it has now been discovered that a one piece implant is able to be inserted into the penis where it circumscribes the penis shaft with the exception of the urethral passage at the six-o'clock penile position. Once placed around the penis, the implant is self-seating, the operating procedure is much shorter than with the two halve implant and the chance of infection has dropped considerably, especially with the addition of an antibacterial material coating on the exterior surfaces of the implant. The details of one or more embodiments of these concepts are set forth in the following description. Other features, objects, and advantages of these concepts will be apparent from the drawings, and from the claims.

BRIEF DESCRIPTION OF THE SEVERAL VIEWS OF THE DRAWING

Like reference symbols in the various drawings indicate like elements.

DETAILED DESCRIPTION

Figure 1:
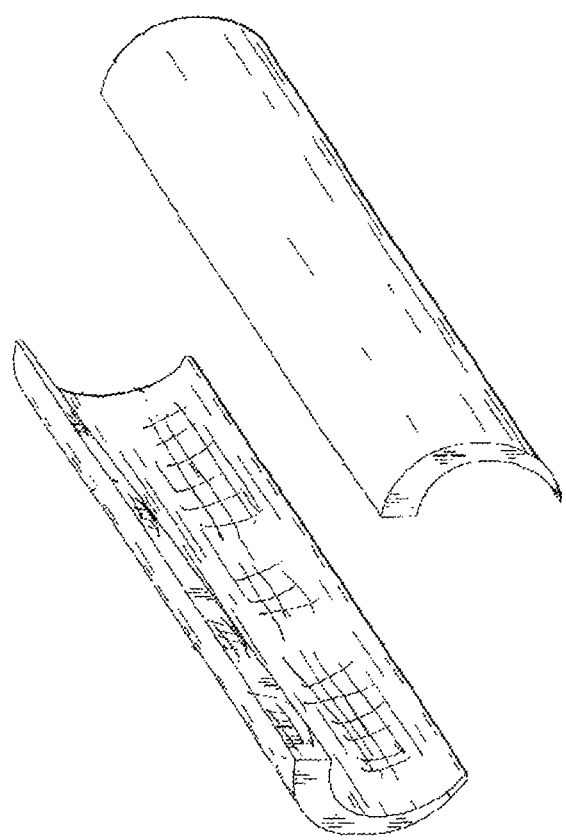
FIG. 1 is an example of a prior art penile implant according to U.S. Pat. No. 6,537,204 issued on Mar. 25, 2003.
Figure 2:
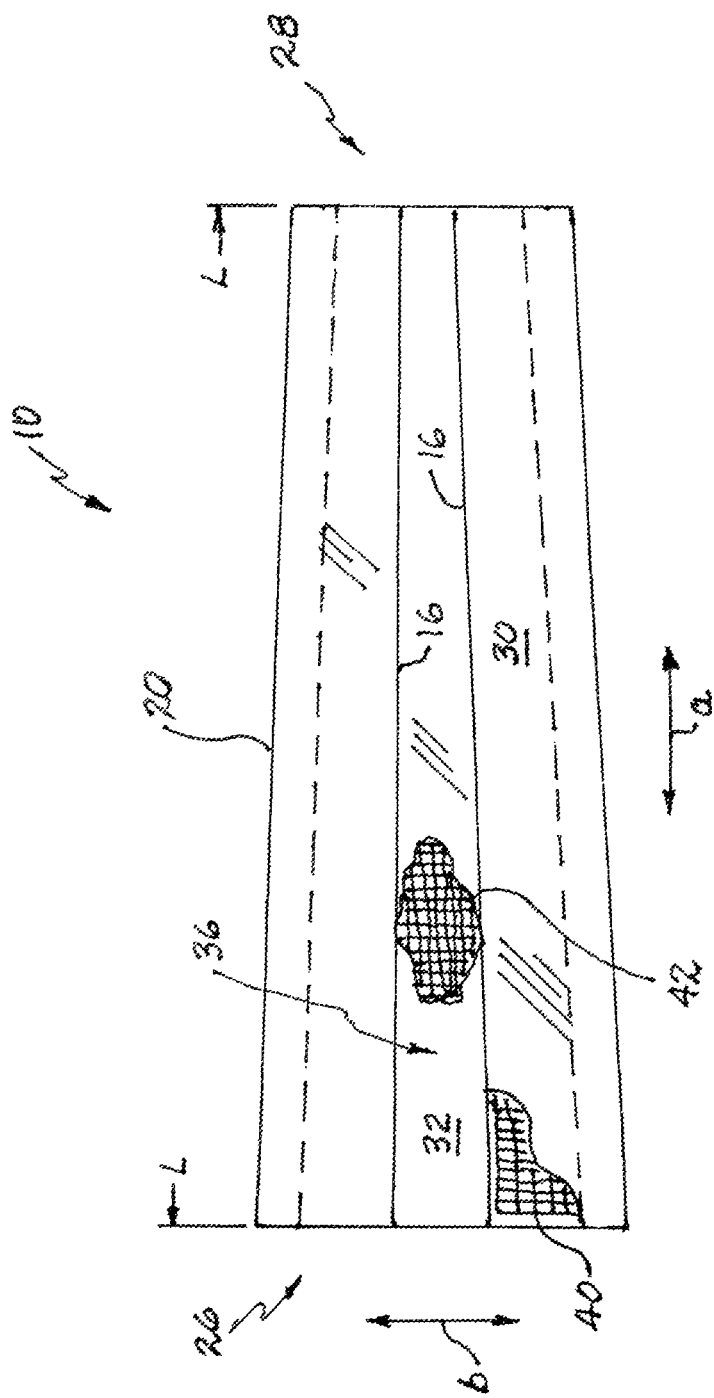
FIG. 2 is an example bottom plan view of the presently described apparatus.
Figure 3:
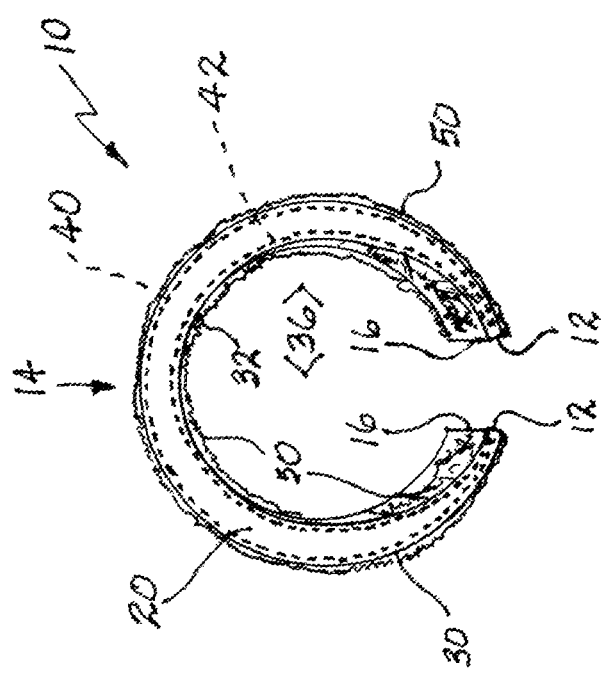
FIG. 3 is an example end view thereof.

FIG. 1 illustrates a prior art penile implant similar to the presently disclosed improved implant 10 illustrated in FIGS. 2 and 3. FIG. 2 shows that implant 10 has a monolithic body 20, that is, a one-piece elongated hollow structural wall which, in the end view of FIG. 3 is seen to be not a full circle but rather is open at its six o'clock position. Implant 10 has a wall thickness which is identified at locations 12 along edges 16. The wall thickness varies smoothly circumferentially from a maximum thickness at a top, twelve o'clock position 14 to a minimum at opposing, spaced apart lower edges 16. Body 20 may be made by molding of silicon rubber into the linear and circular shape shown in the figures. The longitudinal direction, see arrow a, transverse direction, see arrow b are shown in Implant 10 extends between a first larger end 26 and a second smaller end 28, in a smooth linear tapered manner, the ends 26, 28 defining an overall length (shown by arrows L). Implant 10 has an outer exterior surface 30 and an inner exterior surface 32, the latter defining an open space 36 within body 20, which space is accessible through the lower edges 16 which extend the full length L between the first and second ends 26, 28.

When implanted into the penis, implant 10 is placed over and around the shaft of the penis beneath the epithelium (not shown). Implant 10 is custom molded for each individual in accordance with a desired and selected length L and other physical dimensions. Upon implantation, the end 26 implant 10 is positioned adjacent to the recipient's pubic bone and extends to the glans penis at the second end 28 where it is sutured thereto. Between ends 26 and 28 implant 10 tapers from a relatively larger girth at the first end 26 to a relatively smaller girth at the second end 28 a configuration resembling the natural shape of the penis. As shown in FIG. 3, the wall thickness 12 also tapers in mutually coordinated opposing mirror image uniformity from the top position 14 to the lower edges 16. Along the top position 14 longitudinally, wall thickness 12 tapers from a maximum at end 26 of approximately ⅜ inch to a minimum of about 1/16 inch over its length and this may vary from person to person. As stated above, implant 10 may be of silicon rubber or other material that does not trigger rejection by the recipient's immune system. The material is soft with an ASTM D2240 on the Dorometer A scale of not greater than 20. This is quite soft providing a touch to the fingers that is similar to that of the penis itself and yet able to provide a structural rigidity suitable for entry to the vagina upon erection of the penis, structurally rigidized by net sheets 40 as described below.

A first net fabric sheet 40 made of filaments having about 1/32 inch thickness and 1/32 inch spacing is imbedded within the outside exterior surface 30 of body 20 and a similar second net fabric sheet 42 is imbedded within the inside exterior surface 32 of body 20, the sheets 40 and 42 placed just below the surfaces. These sheets 40, 42 therefore are in opposing spaced-apart configurations just below the surfaces of body 20. The net fabric sheets 40, 42 are stretchable in length by between about 2-5% from their relaxed state. In function, sheets 40, 42 provide a restraint on the silicon rubber body 20 which completely prevents creasing. Filaments of 40, 42 are laid out in a rectangular grid with the filaments running in parallel with the longitudinal (a) direction and also with the transverse (b) direction as shown in FIG. 2. This is a critical orientation which avoids steering the penis in either lateral direction.

An antibacterial or antimicrobial compound 50 may be coated over the outer 30 and inner 32 surfaces of body 10 in order to help prevent infection from pathogenic bacteria in or around the surgical site during and after implantation. Such compounds may include: active chlorine, iodine, concentrated alcohols, phenolic substances, cationic surfactants, oxidizers, heavy metals, strong acids, and alkalis.

Embodiments of the subject apparatus and method have been described herein. Nevertheless, it will be understood that various modifications may be made without departing from the spirit and understanding of this disclosure. Accordingly, other embodiments and approaches are within the scope of the following claims.

What is claimed is:
1. A penile implant comprising:
a unitary body having a circular and linearly elongated wall formed around and defining a hollow space;
the unitary body smoothly tapered from a larger outside diameter to a smaller outside diameter between opposing longitudinally spaced apart ends thereof;
the elongated wall tapered diametrically from a thicker top position to thinner longitudinally extensive bottom edges;
the elongated wall having an outside exterior surface and an inside exterior surface;
fabric sheets imbedded in the elongated wall under the outside and inside exterior surfaces; and
wherein said fabric sheets are of a net construction and are flexible and stretchable by between 2 and 5%.
2. The penile implant of claim 1 wherein one of the fabric sheets has a filament spacing not greater than 1/32 inch, whereby the one of the fabric sheets restrains creasing of the unitary body.

\* \* \* \* \*